United States Patent [19]
Poorman

[11] Patent Number: 5,352,901
[45] Date of Patent: Oct. 4, 1994

[54] FORWARD AND BACK SCATTERING LOSS COMPENSATED SMOKE DETECTOR

[75] Inventor: Richard N. Poorman, Columbus, Ind.

[73] Assignee: Cummins Electronics Company, Inc., Columbus, Ind.

[21] Appl. No.: 52,900

[22] Filed: Apr. 26, 1993

[51] Int. Cl.⁵ .................................... G01N 21/49
[52] U.S. Cl. .................... 250/574; 356/343
[58] Field of Search .............. 250/574, 575, 573; 356/343, 342, 338, 336

[56] References Cited

U.S. PATENT DOCUMENTS

| | | |
|---|---|---|
| 3,867,033 | 2/1975 | Hasinger . |
| 3,954,342 | 5/1976 | Boeke . |
| 4,040,743 | 8/1977 | Villaume et al. . |
| 4,126,396 | 11/1978 | Hartmann et al. . |
| 4,166,960 | 9/1979 | Meili . |
| 4,260,883 | 4/1981 | Onoda et al. . |
| 4,420,256 | 12/1983 | Fladda et al. ............... 250/574 X |
| 4,548,500 | 10/1985 | Wyatt et al. . |
| 4,559,813 | 12/1985 | Brekelmans . |
| 4,583,859 | 4/1986 | Hall . |
| 4,647,780 | 3/1987 | Dunkel . |
| 4,649,281 | 3/1987 | Schmitt et al. ............... 250/574 |
| 4,710,025 | 12/1987 | Wyatt et al. ............... 250/574 X |
| 4,719,360 | 1/1988 | Kontani et al. . |
| 4,746,218 | 5/1988 | Lord . |
| 4,769,550 | 9/1988 | Dolnick ............... 250/574 |
| 4,818,705 | 4/1989 | Schneider et al. . |

*Primary Examiner*—David C. Nelms
*Assistant Examiner*—John R. Lee
*Attorney, Agent, or Firm*—Woodward, Emhardt, Naughton, Moriarty & McNett

[57] ABSTRACT

A forward scattering loss compensated smoke sensor or smoke detector and a back scattering loss compensated smoke detector are disclosed. Both systems include first and second light sources for supplying a light signal into a fluid containing particulates. Both systems also include first and second photodetector devices for detecting directly transmitted, forward scattered and/or back scattered light. A ratiometric value or signal is produced in accordance with direct versus scattered detected light levels. The selection of forward versus back scattering particulate detection devices and methods is driven by the efficiency of the scattering which is a function of light source frequencies and particulate size.

17 Claims, 2 Drawing Sheets

FORWARD AND BACK SCATTERING LOSS COMPENSATED SMOKE DETECTOR

FIELD OF THE INVENTION

The present inventions relate to a new and improved construction of optical smoke detectors of the type comprising a radiation source that produces a colimated light beam directed into a fluid and radiation detection devices for detecting light radiation scattered by the particulates suspended in the fluid.

BACKGROUND OF THE INVENTION

Smoke detectors or particulate detectors known in the art project a beam of electromagnetic radiation into a medium or fluid that contains particulates. As the radiation, for instance visible light, infrared or ultraviolet radiation, is scattered by the particulates suspended in the transparent fluid or medium, a measurement of the light scattered away from the colimated beam of light is made using a light detection device. The measurement of the quantity of light scattered by the particulates in the medium provides an indication of the density or quantity of particulates suspended in the fluid.

A particulate or smoke detector known in tile art is shown in Meili, U.S. Pat. No, 4,166,960. Meili discloses a smoke detector including a radiation source that produces a directed radiation beam and a scattered radiation receiver arrangement having directional characteristics. An evaluation circuit is operatively connected with the receiver arrangement for delivering a signal whenever the quantity of scattered light exceeds a predetermined level. The radiation receivers observe two separate fields of view and output signals produced by the receivers are compared with one another.

In view of ever increasing concerns for the health of the environment, it is more desirable of late to measure the quantity of particulates emanating from an internal combustion engine. One such device for detecting particulates in an exhaust stack is disclosed in Dunkel, U.S. Pat. No. 4,647,780. The Dunkel device projects a light beam through an exhaust stack and a photodetector located on the opposite side of the stack from the light beam producing device produces an electronic signal corresponding to the quantity of light that passes through the smoke.

Other devices known to applicant relating to particulate or smoke detection are shown in the following U.S. patents: Schneider et al., U.S. Pat. No. 4,818,705; Boeke, U.S. Pat. No. 3,954,342; Hartmann et al., U.S. Pat. No. 4,126,396; Villaume et al., U.S. Pat. No. 4,040,743; Brekelmans, U.S. Pat. No. 4,559,813; Hasinger, U.S. Pat. No. 4,867,033; Hall, U.S. Pat. No. 4,583,859; Onoda et al., U.S. Pat. No. 4,260,883; Lord, U.S. Pat. No. 4,746,218; Kontani et al., U.S. Pat. No. 4,719,360; and Wyatt et al., U.S. Pat. No. 4,548,500.

None of the devices known to applicant includes a design configuration that properly compensates for variations in the intensity of the light beam projected into the fluid over an extended period of time. In other words, as the light producing device ages or optical components of the system accumulate dirt and grime, the loss of intensity of the light beam results in a steady degradation in the performance of the smoke detection devices shown in the prior art. Thus, a particulate or smoke detection device that compensates for deterioration in performance of the light producing device or transmissivity of the optical components is needed.

SUMMARY OF THE INVENTION

A device for detecting particulate levels in a fluid, in accordance with one aspect of the present invention, comprises a first light source means responsive to signals supplied to a first input to project a first light beam into the fluid, a second light source means responsive to signals supplied to a second input to project a second light beam into the fluid, a first light detector means positioned opposite the first light source means to directly receive the first light beam, the first light detector means producing a first detector signal corresponding to the intensity of light impinging thereon, a second light detector means positioned opposite the second light source means to directly receive the second light beam, the second light detector means producing a second detector signal corresponding to the intensity of light impinging thereon, and a control circuit that supplies a power signal to the first input to activate the first light source means, the control circuit monitoring and comparing the first detector signal and the second detector signal to produce and store a first output signal and a second output signal in accordance therewith, the control circuit also supplying the power signal to the second input to activate the second light source means, the control circuit monitoring and comparing the first and the second detector signals to produce a third output signal and a fourth output signal in accordance therewith, and wherein the first, second, third and fourth output signals are combined to produce a ratiometric value indicative of particulate levels in the fluid.

A method for detecting particulate levels in a fluid according to another aspect of the present invention comprises the steps of providing a first light emitter and a first light detector situated so that a first light beam produced by the first light emitter passes through the fluid before striking the first light detector, providing a second light emitter and a second light detector situated so that a second light beam produced by the second light emitter passes through the fluid before striking the second light detector, locating the first light emitter and the second light emitter so that the first light beam and the second light beam are substantially planar, exciting the first light emitter to produce the first light beam and measuring the response produced by the first and the second light detectors as a first detected signal and a second detected signal, exciting the second light emitter to produce the second light beam and measuring the response produced by the first and the second light detectors as a third detected signal and a fourth detected signal, and combining the first, second, third and fourth detected signals to produce a value representative of the opacity of the fluid.

One object of the present invention is to provide an improved smoke detector device.

Another object of the present invention is to provide a forward scattering or back scattering loss compensated smoke detector wherein loss of transmissivity of the optical components or variations in the intensity of light produced by a light source does not affect the accuracy of the system over time.

Yet another object of the present invention is to provide a means for separating the control circuitry, light producing devices, and photodetectors a short distance from the fluid duct in which the particulate laden fluid moves.

Still another object of the present invention is to provide a forward scattering or back scattering loss compensated smoke detector wherein the light that is directly transmitted through a fluid is measured and compared with the quantity of light that is scattered by the fluid at an angle or position offset from the direct transmission axis of the light beam in order to provide a ratiometric value corresponding to opacity of the fluid.

These and other objects of the present invention will become more apparent from the following description of the preferred embodiments.

DESCRIPTION OF THE PREFERRED EMBODIMENTS

Figure 1:
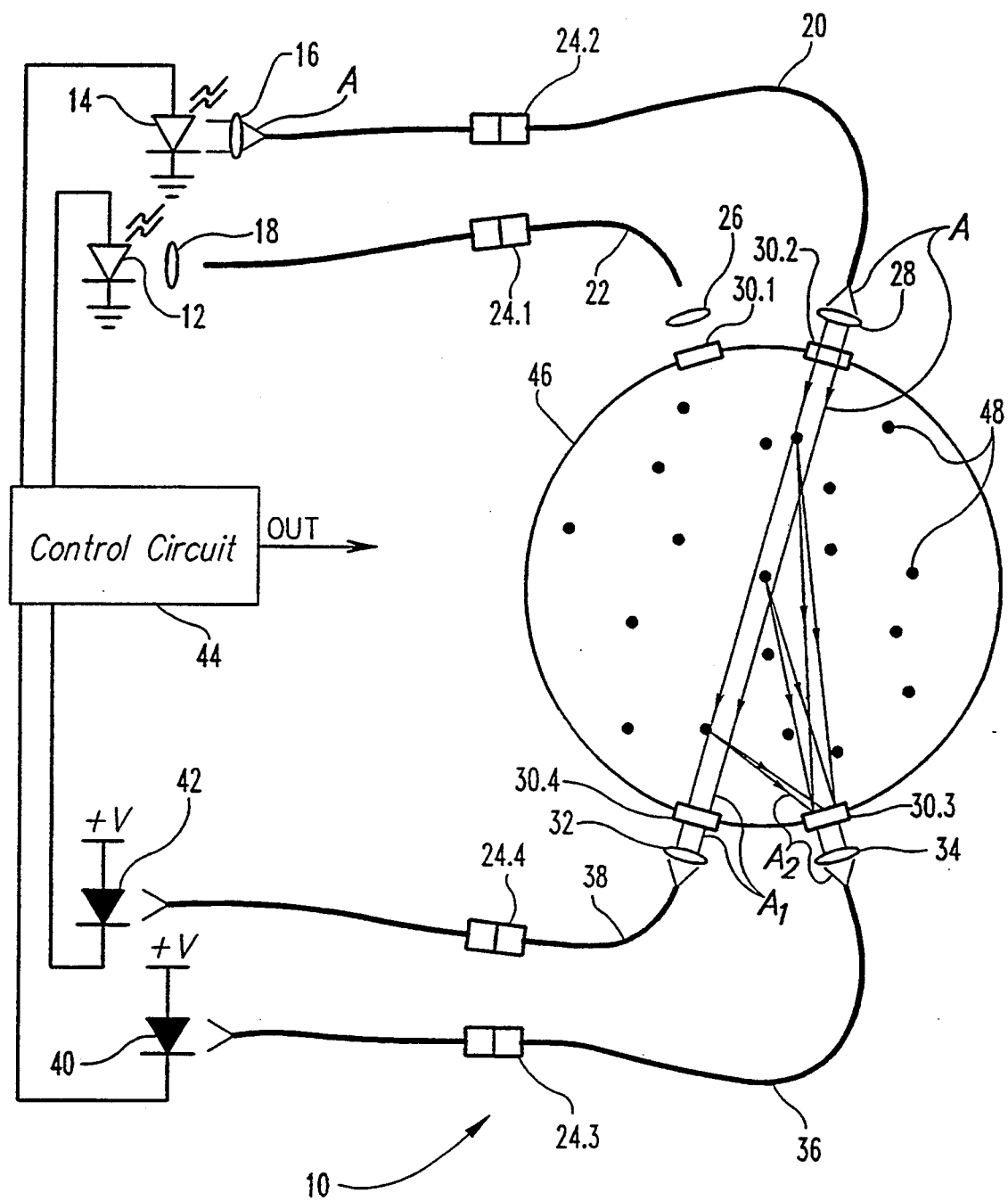
FIG. 1 is a diagrammatic illustration of a forward scattering loss compensated smoke detector system according to the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to FIG. 1, a forward scattering loss compensated smoke detector 10 according to the present invention is shown. The detector system 10 includes the following components: light emitting diodes 12 and 14 (LEDS), focusing lenses 16 and 18, fiber optic cables 20 and 22, fiber optic connectors 24.1, 24.2, 24.3, and 24.4, focusing lenses 26 and 28, transparent windows 30.1, 30.2, 30.3 and 30.4, focusing lenses 32 and 34, fiber optic cables 36 and 38, photodetector devices 40 and 42 and control circuit 44.

Smoke detector 10 operates in accordance with the following functional description. Smoke Detector 10 uses two light sources 12 and 14 and two light detectors or photodetectors 40 and 42. Four fiber optic links or cables 20, 22, 36 and 38 provide a means for separating the light sources 12 and 14 and the photodetectors or light detectors 40 and 42 a safe distance from the hot exhaust stack 46. In the diagrammatic illustration shown, the exhaust stack 46 is shown from a top view or plan view looking directly downward into the exhaust stack. The smoke sensor or detector 10 observes a cross-section of the exhaust stack or pipe 46 with four optic windows 30.1, 30.2, 30.3, 30.4 situated at predetermined locations, preferably in a planar arrangement perpendicular to pipe 46. Lenses 16 and 18 focus light beams produced by light sources 14 and 12, respectively, into optical cables 20 and 22, respectively. Lens 26 disperses the light signal carried by fiber optic cable 22 into a colimated beam of light directed towards lens 34 and fiber optic cable 36. Likewise, lens 28 bends or alters the light beam A carried by optic cable 20 into an expanded colimated beam of light that is directed towards lens 32 and fiber optic cable 38. Light from cables 36 and 38 is supplied to photodetectors 40 and 42, respectively. Control circuit 44 is connected to detectors 40 and 42 to monitor the signals produced by detectors 40 and 42 representative of the intensity of light impinging on each detector. Control circuit 44 also provides individually controllable excitation signals to light sources 12 and 14. An output signal is produced by control circuit 44 representative of the opacity of the exhaust fluid within exhaust stack 46 resulting from the presence of particulates 48.

The smoke detector 10 operates in a two step sequence to acquire signals from detectors 40 and 42. In the first step, circuit 44 supplies a power signal to LED 14 and the combination of lens 16, fiber optic cable 20, connector 24.2, and lens 28 provide a medium by which the light A produced by LED 14 is supplied or routed to transparent window 30.2 and colimated into a beam for transmission through window 30.2 situated in exhaust stack 46. The light beam A passes through window 30.2, stack 46 containing engine exhaust and window 30.4 wherein some of the light is scattered by smoke particles 48. The light beam A, proceeding directly through the exhaust stack 46 from cable 20 passes through window 30.4 and is collected by lens 32 and focused onto optic cable 38. Cable 38 and connector 24.4 provide an optical conduit for transmitting or conveying the light signal $A_1$ to photodetector 42. Light that is scattered by the particulates 48 within the exhaust stack 46 passes through window 30.3 and is focused onto the fiber optic cable 36 by lens 34. Cable 36 and connector 24.3 provide a path for transmitting the scattered light signal $A_2$ to the photodetector 40. Photodetector 40 provides a signal to control circuit 44 representative of and corresponding to the intensity of the scattered light signal or light beam $A_2$.

Subsequently, control circuit 44 extinguishes the power signal to light source 14 and simultaneously provides an excitation signal to light source 12. In like fashion as previously described, the optical path components including lens 18, fiber optic cable 22, connector 24.1, and lens 26 transmit the light signal from light source 12 into the exhaust stack 46. In this stage of the analysis, the direct path through the exhaust stack is from fiber optic cable 22 through lens 26 into lens 34 and fiber optic cable 36. The light that is transmitted directly through the exhaust stream is represented by a voltage signal produced by photodetector 40. The signal is supplied to an input of circuit 44. Similarly, scattered light signals are collected by lens 32 and focused onto optical cable 38 wherein photodetector 42 provides a corresponding voltage signal indicative of the scattered light intensity. Control circuit 44 receives the direct and scattered light intensity signals from photodetectors 40 and 42, respectively, in this step of the analysis.

Thus, when light source 14 provides the light excitation signal, voltages $V_1$ and $V_2$ are produced ($V_1$ represents the direct transmitted light and $V_2$ represents the scattered light measured while light source 14 is activated). Similarly, when light source 12 is activated and light source 14 is deactivated, the directly transmitted light signal produced by photodetector 40 is designated by voltage $V_4$ and the scattered light signal voltage produced by photodetector 42 is designated $V_3$. In accordance therewith, the following formulas and definitions of variables used therein provide the basis for the relationship that opacity is proportional to the product of the scattered light signals divided by the product of the intensities of the directly transmitted light signals, particularly when the light beams passing through the fluid are situated in the same plane.

Consider:

$$\text{Opacity} \propto \sqrt{\frac{V_2 * V_3}{V_1 * V_4}}$$

where:

$V_1 \propto (L_{14}, I_{16}, E_{20}, C_{24.2}, O_{28}, W_{30.2}, T_1, W_{30.4}, O_{32}, C_{24.4}, E_{38}, D_{42})$ $V_2 \propto (L_{14}, I_{16}, E_{20}, C_{24.2}, O_{28}, W_{30.2}, S_1, W_{30.3}, O_{34}, C_{24.3}, E_{36}, D_{40})$ $V_3 \propto (L_{12}, I_{18}, E_{22}, C_{24.1}, O_{26}, W_{30.1}, S_2, W_{30.4}, O_{32}, C_{24.4}, E_{38}, D_{42})$ $V_4 \propto (L_{12}, I_{18}, E_{22}, C_{24.1}, O_{26}, W_{30.1}, T_2, W_{30.3}, O_{34}, C_{24.3}, E_{36}, D_{40})$ and where:
- $L_x$ = Light source intensity
- $I_x$ = Injection efficiency of light into the fiber
- $E_x$ = Efficiency of transmission fiber
- $C_x$ = Connector coupling efficiency
- $O_x$ = Transmission coefficients of the optics
- $W_x$ = Transmission coefficients of the windows
- $T_1, T_2$ = Transmission efficiency of the light through the smoke
- $S_1, S_2$ = Scattering coefficient of collected light Making substitutions according to the above known relationships, all terms cancel resulting in:

$$\text{Opacity} \propto \sqrt{\frac{S_1 * S_2}{T_1 * T_2}}$$

Geometry can make $S_1 = S_2$ and $T_1 = T_2$. The smoke is proportional to the quantity $(S_x/T_x)$ and independent of the influences from the optic paths.

Figure 2:
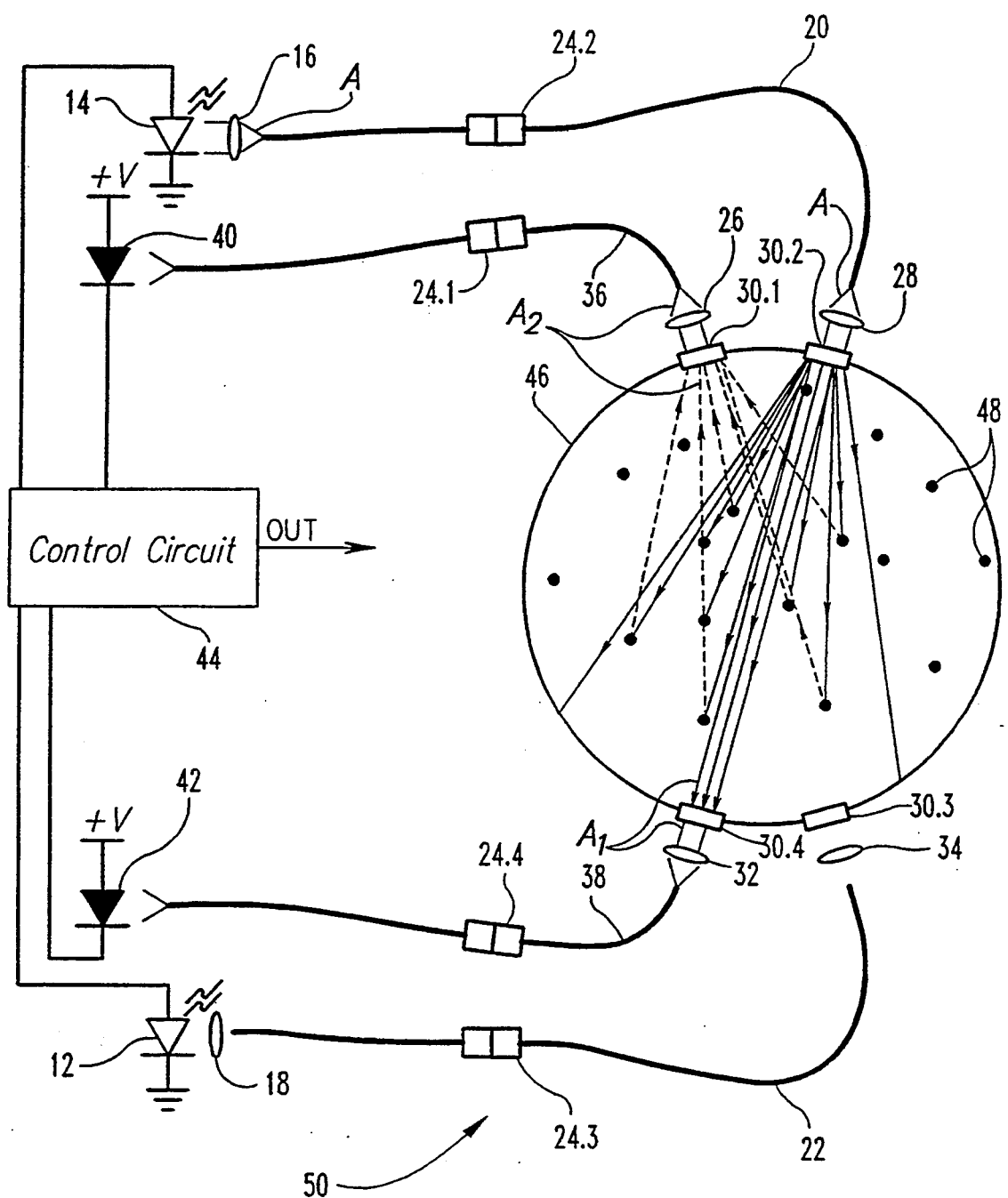
FIG. 2 is a diagrammatic illustration of a back scattering loss compensated smoke detector system according to the present invention.

Referring now to FIG. 2, another embodiment of the present invention, a back scattering loss compensated smoke detector 50, is shown. Smoke detector or smoke sensor 50 includes the identical complement of components as the sensor 10 of FIG. 1 with the exception being the rearrangement of certain components so that the scattered light measured by the system is light that is "back scattered" versus the measurement of "forward scattered" light as in the system 10 of FIG. 1. All identical components are indicated with like numerals or reference identifiers.

Operationally speaking, control circuit 44 energizes light source or LED 14 to produce a light signal A and lens 16 focuses the light signal A from light source 14 onto optical cable 20 which includes a fiber optic connector 24.2. Cable 20 supplies the light signal to lens 28 wherein the light signal is focused into an expanded beam and transmitted through window 30.2 into the exhaust stack 46. Smoke particulates 48 in the exhaust stack 46 interfere with direct transmission of the light beam from lens 28 to lens 32. Directly transmitted light beam $A_1$ passes through the exhaust stack 46 and through window 30.4 and lens 32. Lens 32 focuses the light beam $A_1$ onto fiber optic cable 38 and the light signal $A_1$ is subsequently supplied to photodetector 42. Simultaneously, light beam $A_2$ is reflected or scattered backwards through window 30.1 and towards lens 26 by particulates 48. Lens 26 focuses the scattered light $A_2$ onto fiber optic cable 36. Fiber optic cable 36 supplies the scattered light signal to photodetector 40. Control circuit 44 stores the direct light transmitted signal from photodetector 42 as voltage $V_1$. The back scattered light $A_2$ supplied to photodetector 40 and is stored by control circuit 44 as voltage $V_2$.

Subsequently, control circuit 44 extinguishes the signal to LED 14 and provides an excitation signal to LED 12. The light produced by LED 12 is focused onto optical cable 22 by lens 18 and subsequently is focused into an expanded beam by lens 34 and transmitted through window 30.3 towards lens 26. Thus, in this step, light that is directly transmitted through exhaust stack 46 is collected by lens 26 and focused onto fiber optic cable 36. The light from fiber optic cable 36 is supplied to photodetector 40 and control circuit 44 stores a voltage $V_4$ corresponding to the intensity of light striking photodetector 40. In similar fashion, light (not shown) reflected by particulates 48 is collected by lens 32 and focused onto fiber optic cable 38. Likewise, the back scattered light passing through cable 38 is supplied to photodetector 42 and control circuit 44 stores a voltage $V_3$ corresponding to the signal produced by detector 42. Control circuit 44 compares the voltages $V_1$, $V_2$, $V_3$ and $V_4$ to produce an output signal representative of the opacity of the fluid within exhaust stack 46. The relationships previously set forth describing opacity and the variables which affect the voltages produced by the photodetectors are equally applicable to the system 50 shown in FIG. 2. The exception being that the $S_1$ and $S_2$ factors described as the scattering coefficients of collected light are replaced by $B_1$ and $B_2$ variables representing the "back scattering" coefficients of reflected light $A_2$ in the system 50.

Again Consider:

$$\text{Opacity} \propto \sqrt{\frac{V_2 * V_3}{V_1 * V_4}}$$

where:

$V_1 \propto (L_{14}, I_{16}, E_{20}, C_{24.2}, O_{28}, W_{30.2}, T_1, W_{30.4}, O_{32}, C_{24.4}, E_{38}, D_{42})$ $V_2 \propto (L_{14}, I_{16}, E_{20}, C_{24.2}, O_{28}, W_{30.2}, B_1, W_{30.1}, O_{26}, C_{24.1}, E_{36}, D_{40})$ $V_3 \propto (L_{12}, I_{18}, E_{22}, C_{24.3}, O_{34}, W_{30.3}, B_2, W_{30.4}, O_{32}, C_{24.4}, E_{38}, D_{42})$ $V_4 \propto (L_{12}, I_{18}, E_{22}, C_{24.3}, O_{34}, W_{30.3}, T_2, W_{30.1}, O_{26}, C_{24.1}, E_{36}, D_{40})$ and:
- $L_x$ = Light source intensity
- $I_x$ = Injection efficiency of light into the fiber
- $E_x$ = Efficiency of transmission fiber
- $C_x$ = Connector coupling efficiency
- $O_x$ = Transmission coefficients of the optics
- $W_x$ = Transmission coefficients of the windows
- $T_1, T_2$ = Transmission efficiency of the light through the smoke
- $B_1, B_2$ = Backscattering coefficient of reflected light from the smoke Making substitutions into the equations in-accordance with the relationships set forth above, all terms cancel except the following which define opacity:

$$\text{Opacity} \propto \sqrt{\frac{B_1 * B_2}{T_1 * T_2}}$$

Thus, it can be shown that the physical geometry of the system can be arranged to make $B_1 = B_2$ and $T_1 = T_2$. The result is the smoke quantity is proportional to B over T and independent of the influences from the optic paths or the intensity of the light produced by the light sources.

It is known that particle size relative to wavelength of light affects the direction of light scattering. As the particle size increases with a fixed light frequency, an increase in the angle of reflection takes place. When the particle size exceeds a certain threshold given a fixed light frequency, it is known that more light is reflected back towards the source than that light scattered slightly away from the direct transmission axis. One skilled in the art of particle detecting devices will select an angular relationship between the directly transmitted light beams shown in FIGS. 1 and 2 in accordance with the above known principles.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A device for detecting particulate levels in a fluid, said device comprising:
    a first light source responsive to signals supplied to a first input to project a first light beam into the fluid;
    a second light source responsive to signals supplied to a second input to project a second light beam into the fluid;
    a first light detector positioned opposite said first light source to directly receive said first light beam, said first light detector producing a first detector signal corresponding to the intensity of light impinging thereon;
    a second light detector positioned opposite said second light source to directly receive said second light beam, said second light detector producing a second detector signal corresponding to the intensity of light impinging thereon; and
    a control circuit that supplies a power signal to said first input to activate said first light source, said control circuit monitoring and comparing said first detector signal and said second detector signal to produce and store a first output signal and a second output signal, respectively, in accordance therewith, said control circuit also supplying said power signal to said second input to activate said second light source, said control circuit monitoring and comparing said first and second detector signals to produce a third output signal and a fourth output signal, respectively, in accordance therewith, and wherein said first, second, third and fourth output signals are combined to produce a ratiometric value indicative of particulate levels in the fluid.

2. The device of claim 1 wherein said said first and said second light detectors are positioned so that forward scattered light from said first or second light beams strikes said second and said first light detectors, respectively.

3. The device of claim 2 including first and second fiber optic means situated between said first and second light sources and said fluid, respectively, to facilitate situating said first and second light sources remotely from said fluid.

4. The device of claim 3 including third and fourth fiber optic means situated between said fluid and said first and second light detectors, respectively, to facilitate situating said first and second light detectors remotely from said fluid.

5. The device of claim 4 wherein each of said first and second light sources includes a light emitting diode for producing light and a focusing means for injecting light emitted by said light emitting diodes into said first and second fiber optic means.

6. The device of claim 5 wherein said first, said second, said third, and said fourth fiber optic means each include a fiber optic connector situated in series with each of said fiber optic means thereby enabling removable connection of said fiber optic means.

7. The device of claim 1 wherein said second light detector is situated to receive back scattered light from said first light source and said first light detector is situated to receive back scattered light from said second light source.

8. The device of claim 7 including first and second fiber optic means situated between said first and second light sources and said fluid, respectively, to facilitate situating said first and second light sources remotely from said fluid.

9. The device of claim 8 including third and fourth fiber optic means situated between said fluid and said first and second light detectors, respectively, to facilitate situating said first and second light detectors remotely from said fluid.

10. The device of claim 9 wherein each of said first and second light sources includes a light emitting diode for producing light and a focusing means for injecting said light emitted by said light emitting diode into said first and second fiber optic means, respectively.

11. The device of claim 10 wherein said first, said second, said third, and said fourth fiber optic means each include a fiber optic connector situated in series with each of said fiber optic means thereby enabling removable connection of said fiber optic means.

12. The device of claim 7 wherein said first light detector and said second light source are situated in close proximity to one another and wherein said second light detector and said first light source are situated in close proximity to one another.

13. The device of claim 1 wherein said first light detector, said second light detector, said first light source and said second light source are situated substantially in a plane perpendicular to the flow of the fluid.

14. The device of claim 1 wherein said ratiometric value is an opacity factor determined by taking the square root of the following value: the product of said second and said third output signals divided by the product of said first and said fourth output signals.

15. A device for detecting particulate levels in a fluid, said device comprising:
    a first light source means responsive to signals supplied to a first input to project a first light beam into the fluid;
    a second light source means responsive to signals supplied to a second input to project a second light beam into the fluid;
    a first light detector means positioned opposite said first light source means to directly receive said first light beam, said first light detector means producing a first detector signal corresponding to the intensity of light impinging thereon;
    a second light detector means positioned opposite said second light source means to directly receive said second light beam, said second light detector means producing a second detector signal corresponding to the intensity of light impinging thereon; and a control circuit that supplies a power signal to said first input to activate said first light source means, said control circuit monitoring and comparing said first detector signal and said second detector signal to produce and store a first output signal and a second output signal in accordance therewith, said control circuit also supplying said power signal to said second input to activate said second light source means, said control circuit monitoring and comparing said first and said second detector signals to produce a third output signal and a fourth output signal in accordance therewith, and wherein said first, second, third and fourth output signals are combined to produce a ratiometric value indicative of particulate levels in the fluid.

16. A smoke particulate detection device for measuring particulate emissions in an exhaust stream comprising:

first light source means for producing a first light signal in response to a first activation signal;

second light source means for producing a second light signal in response to a second activation signal;

first focusing means for optically concentrating said first light signal into a first concentrated light beam;

second focusing means for optically concentrating said first light signal into a second narrow light beam;

first fiber optic means for providing an optical conduit over which said first narrow light beam is conveyed from said first focusing means to a first location adjacent the exhaust stream;

second fiber optic means for providing an optical conduit over which said second concentrated light beam is conveyed from said second light source to a second location adjacent the exhaust stream;

first beam expanding means for spreading said first concentrated light beam into a first expanded light beam and conveying said first expanded light beam into said exhaust stream along a first path;

second beam expanding means for spreading said second concentrated light beam into a second expanded light beam and conveying said second expanded light beam into said exhaust stream along a second path;

third focusing means situated in the path of said first expanded light beam for focusing a portion of said first expanded light beam into a first direct light signal;

fourth focusing means situated in the path of said second expanded light beam for focusing a portion of said second expanded light beam into a second direct light signal;

first photodetector means for producing a first electrical signal corresponding to the intensity of light impinging on said first photodetector;

second photodetector means for producing a second electrical signal corresponding to the intensity of light impinging on said second photodetector;

third fiber optic means situated adjacent said third focusing means for providing an optical conduit over which said first direct light signal is guided to said first photodetector means;

fourth fiber optic means situated adjacent said fourth focusing means for providing an optical conduit over which said second direct light signal is guided to said second photodetector means; and circuit means for supplying said first activation signal to said first light source means and comparing the output from said first and second photodetector devices to produce a first ratiometric value representative of particulate levels in the exhaust stream, said circuit means also supplying said second activation signal to said second light source means and comparing the output from said first and second photodetector devices while said first light source means is inactive to produce a second ratiometric value representative of particulate levels in the exhaust stream, and wherein said first and second ratiometric values are combined to produce a value indicative of particulate levels in the exhaust stream.

17. A method for detecting particulate levels in a fluid comprising the steps of:

providing a first light emitter and a first light detector situated so that a first light beam produced by said first light emitter passes through said fluid before striking said first light detector;

providing a second light emitter and a second light detector situated so that a second light beam produced by said second light emitter passes through said fluid before striking said second light detector;

locating said first light emitter and said second light emitter so that said first light beam and said second light beam are substantially planar;

exciting said first light emitter to produce said first light beam and measuring the response produced by said first and said second light detectors as a first detected signal and a second detected signal;

exciting said second light emitter to produce said second light beam and measuring the response produced by said first and said second light detectors as a third detected signal and a fourth detected signal; and combining said first, second, third and fourth detected signals to produce a value representative of the opacity of the fluid.

* * * * *

UNITED STATES PATENT AND TRADEMARK OFFICE
CERTIFICATE OF CORRECTION

PATENT NO. : 5,352,901

DATED : October 4, 1994

INVENTOR(S) : Richard N. Poorman

It is certified that error appears in the above-indentified patent and that said Letters Patent is hereby corrected as shown below:

In Column 5, at line 4, add --Opacity = $f(V_1, V_2, V_3, V_4)$--.

In Column 6, at line 33 add --Opacity = $f(V_1, V_2, V_3, V_4)$--.

Signed and Sealed this

Sixth Day of December, 1994

BRUCE LEHMAN

Attest:

Attesting Officer

Commissioner of Patents and Trademarks